United States Patent
Chang et al.

(10) Patent No.: US 10,299,663 B2
(45) Date of Patent: May 28, 2019

(54) WIDE-ANGLE ILLUMINATION DEVICE

(71) Applicant: VIVOTEK INC., New Taipei (TW)

(72) Inventors: Chih-Hung Chang, New Taipei (TW);
Yi-Hsin Yeh, New Taipei (TW)

(73) Assignee: VIVOTEK INC., New Taipei (TW)

( * ) Notice: Subject to any disclaimer, the term of this patent is extended or adjusted under 35 U.S.C. 154(b) by 0 days.

(21) Appl. No.: 15/862,645

(22) Filed: Jan. 5, 2018

(65) Prior Publication Data

US 2018/0192856 A1   Jul. 12, 2018

(30) Foreign Application Priority Data

Jan. 10, 2017   (TW) .............................. 106100670 A (51) Int. Cl.
| | |
|---|---|
| *F21V 7/04* | (2006.01) |
| *A61B 1/00* | (2006.01) |
| *G02F 1/13357* | (2006.01) |
| *G02B 13/06* | (2006.01) |
| *F21V 8/00* | (2006.01) |
| *A61B 1/06* | (2006.01) |
| *G02B 9/64* | (2006.01) |
| *F21V 7/00* | (2006.01) |
| *F21V 7/09* | (2006.01) |

(Continued)

(52) U.S. Cl.
CPC .......... *A61B 1/00174* (2013.01); *A61B 1/063* (2013.01); *F21V 7/0083* (2013.01); *F21V 7/04* (2013.01); *F21V 7/09* (2013.01); *G02B 6/0043* (2013.01); *G02B 9/64* (2013.01); *G02B 13/06* (2013.01); *G02F 1/1336* (2013.01); *F21Y 2103/00* (2013.01); *G03B 37/06* (2013.01); *G03B 2215/0567* (2013.01)

(58) Field of Classification Search
CPC ..... A61B 1/00174; A61B 1/063; A61B 13/06; F21V 7/0083; G02F 1/1336; G02B 9/64; G02B 37/06; G03B 2215/0567; F21Y 2103/00
See application file for complete search history.

(56) References Cited

U.S. PATENT DOCUMENTS

| | | | | |
|---|---|---|---|---|
| 2009/0027883 A1* | 1/2009 | Koike | ..................... | F21S 8/086 |
| | | | | 362/235 |
| 2010/0315810 A1* | 12/2010 | Tseng | ..................... | F21V 14/02 |
| | | | | 362/234 |
| 2016/0356451 A1* | 12/2016 | Lin | ......................... | F21V 5/04 |

FOREIGN PATENT DOCUMENTS

| | | |
|---|---|---|
| CN | 202812925 U | 3/2013 |
| EP | 2 645 434 A1 | 10/2013 |
| TW | M456039 U1 | 6/2013 |

* cited by examiner

*Primary Examiner* — Ali Alavi
(74) *Attorney, Agent, or Firm* — Winston Hsu (57) ABSTRACT

A wide-angle illumination device includes a base, a first light guiding module and two second light guiding modules. The base includes a central region and two lateral regions, and the two lateral regions are respectively located on opposite positions of the central region. A first light emitting module is disposed on the central region, and two second light emitting modules are disposed on the two lateral regions. The first light guiding module is disposed on the central region and matched with the first light emitting module, to guide a first optical signal of the first light emitting module toward a front of the base. The two second light guiding modules are disposed on the lateral regions and matched with the second light emitting modules, to guide a second optical signal of the second light emitting module out of an end of the base.

14 Claims, 6 Drawing Sheets

(51) Int. Cl.
*F21Y 103/00* (2016.01)
*G03B 37/06* (2006.01)

WIDE-ANGLE ILLUMINATION DEVICE

BACKGROUND OF THE INVENTION

1. Field of the Invention

The present invention relates to an illumination device, and more particularly, to a wide-angle illumination device having the 180-degree irradiation range.

2. Description of the Prior Art

A monitoring apparatus usually has one or more camera lenses; each lens has a specific field of view, and the monitoring apparatus can utilize the camera lenses arranged around to achieve an aim of wide-angle photography. For providing the high quality wide-angle image, the conventional monitoring apparatus has an illuminating device disposed by each camera lens for light compensation while the monitoring apparatus is operated in a dark environment, which means the illuminating device can provide extra suitable irradiation to make the camera lens capture the superior image. However, the conventional monitoring apparatus needs several illuminating devices matched with the camera lenses, and results in drawbacks of expensive hardware cost and difficult assembling procedures.

SUMMARY OF THE INVENTION

The present invention provides a wide-angle illumination device having the 180-degree irradiation range for solving above drawbacks.

According to the claimed invention, a wide-angle illumination device includes a base, a first light guiding module and two second light guiding modules. The base has a central region and two lateral regions; the two lateral regions are respectively disposed on opposite positions around the central region. A first light emitting module is disposed on the central region, and two second light emitting modules are respectively disposed on the two lateral regions. The first light guiding module is disposed on the central region and matched with the first light emitting module, so as to guide a first optical signal emitted by the first light emitting module toward a front of the base. The two second light guiding modules are disposed on the two lateral regions and respectively matched with the second light emitting modules. Each of the two second light guiding modules is utilized to guide a second optical signal emitted by a corresponding second light emitting module out of an end of the base. An amount of irradiation ranges of the first light guiding module and the two second light guiding modules is equal to or greater than 180 degrees.

According to the claimed invention, the wide-angle illumination device further includes a third light guiding module disposed on the base and covering the central region and the two lateral regions, and utilized to constrain irradiation ranges of the first optical signal and the second optical signal along two sides of the base. The base, the first light guiding module, the two second light guiding modules and the third light guiding module are monolithically integrated with each other.

The wide-angle illumination device of the present invention can utilize the first light guiding module and the second light guiding module having dissimilar irradiation ranges to guide the optical signals emitted by the first light emitting module and the second light emitting module respectively toward different irradiation angles and ranges. For example, the two first light guiding sub-components in middle of the first light guiding module can have the wider irradiation range mainly utilized to fill light in the central region via diffusion; the two first light guiding sub-components at the sides can have the gathered irradiation range utilized to slightly compensate the light in the central region; the second light guiding module can have the irradiation range focused on two ends of the base, so that the central region is slightly irradiated to form the uniform irradiation range equal to or greater than one hundred and eighty degrees on a single plane (which means the front above the base) along the longitudinally structural direction of the base. The present invention uses the single wide-angle illumination device to form the large scale irradiation range, and has no drawbacks of complicated light distribution, expensive hardware cost and difficult assembling procedures of the conventional illuminating device.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
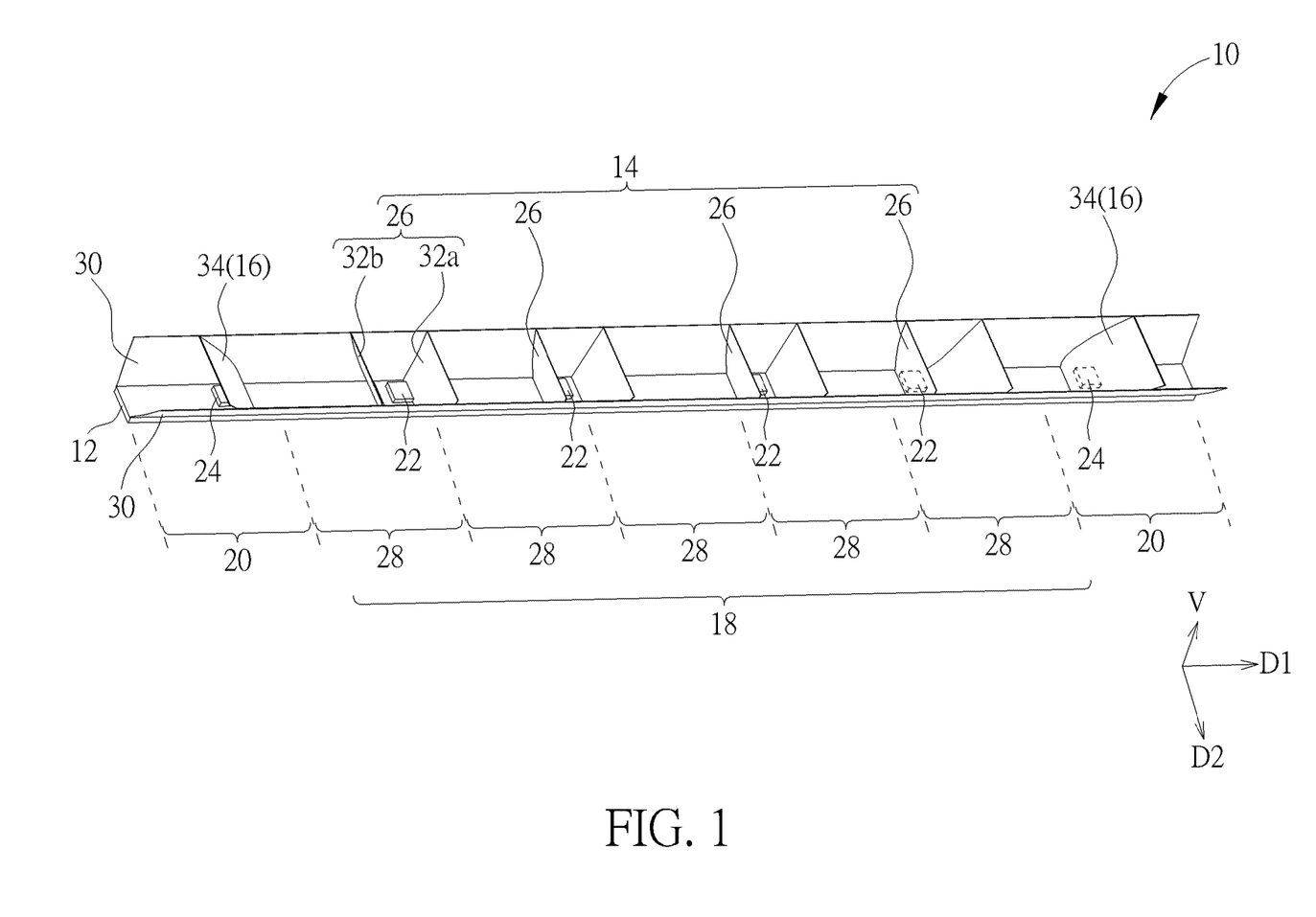
FIG. 1 and FIG. 2 respectively are diagrams of a wide-angle illumination device in different views according to a first embodiment of the present invention.
Figure 2:
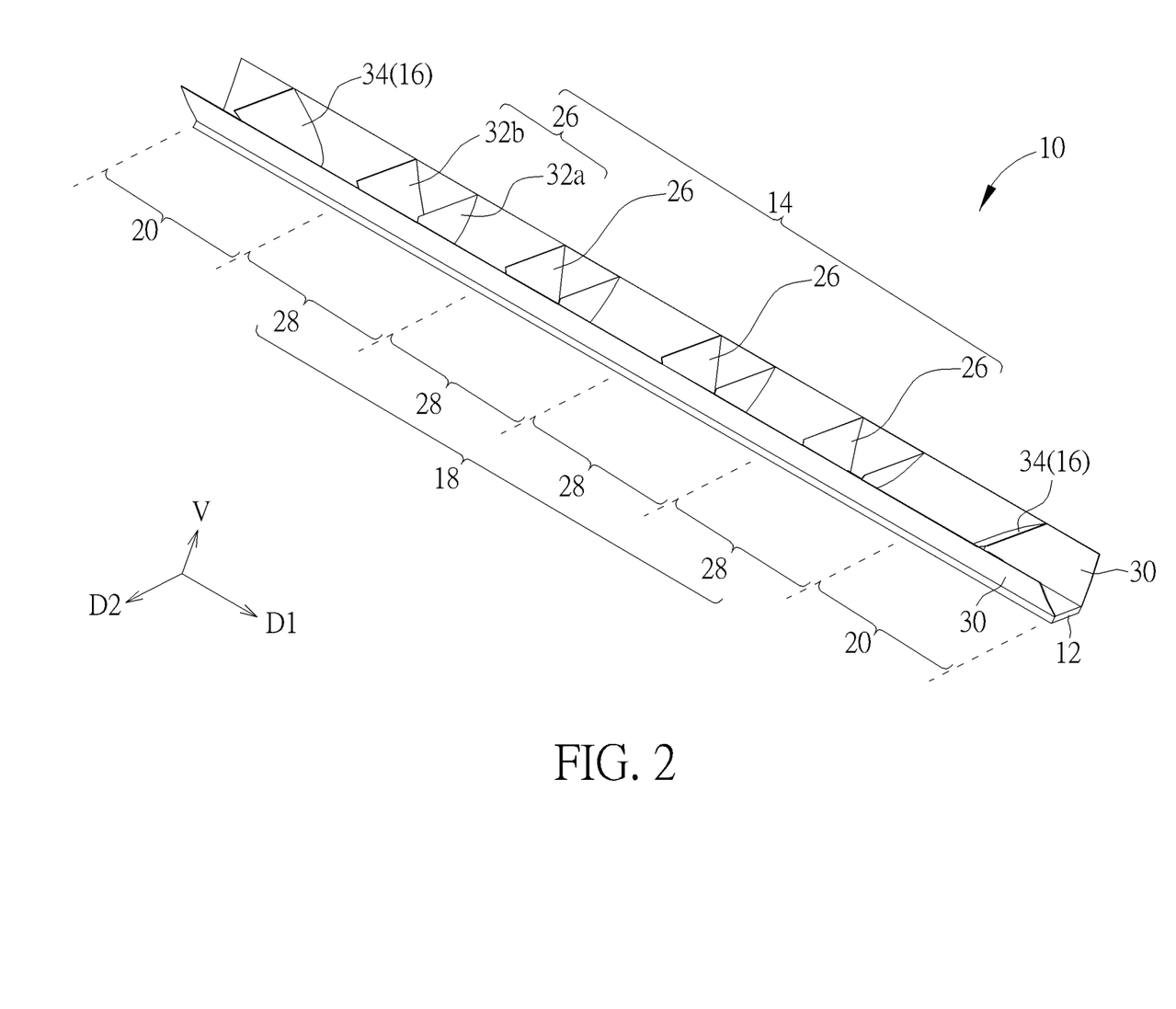
Figure 3:
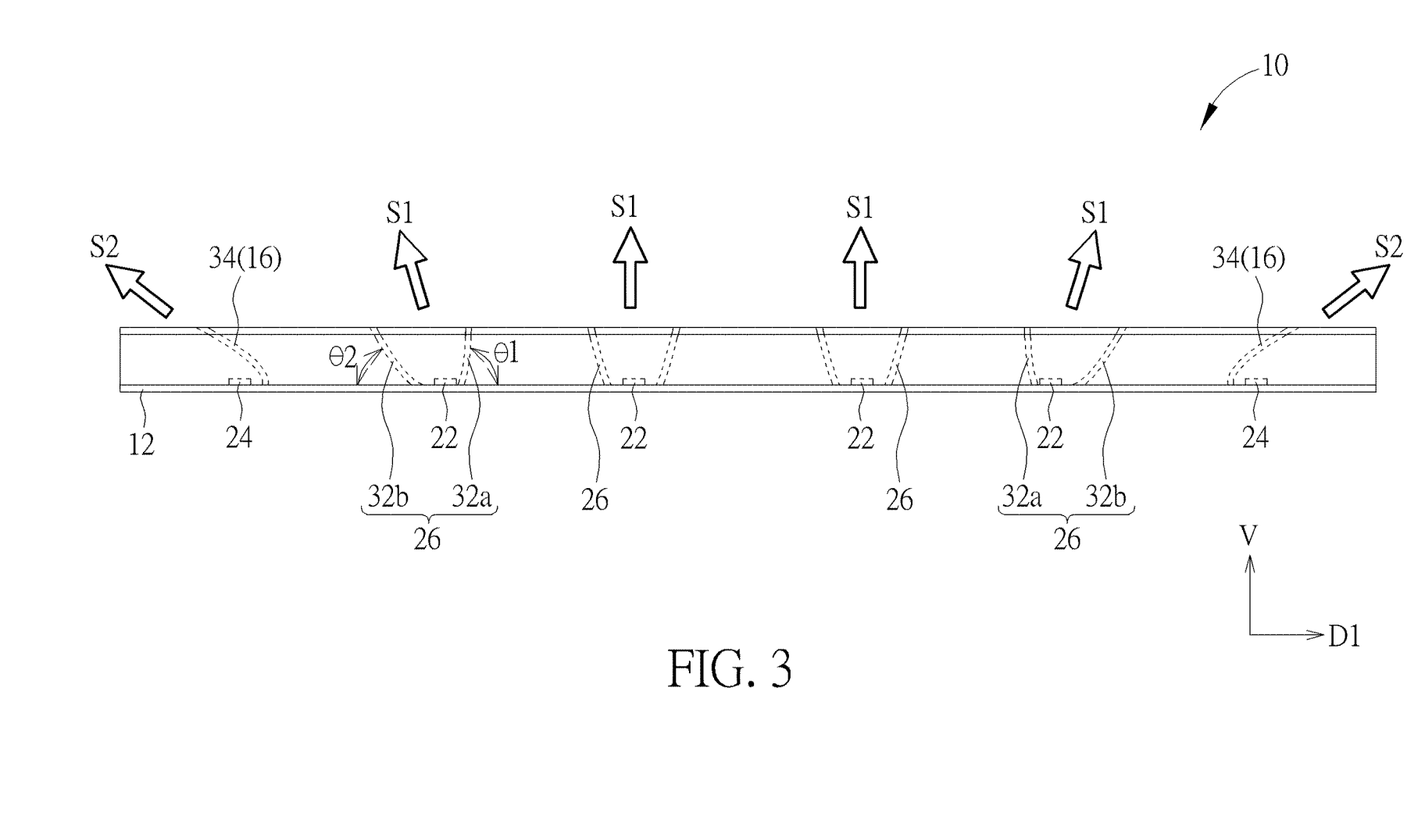
FIG. 3 is a sectional view of the wide-angle illumination device according to the first embodiment of the present invention.

Please refer to FIG. 1 to FIG. 3. FIG. 1 and FIG. 2 respectively are diagrams of a wide-angle illumination device 10 in different views according to a first embodiment of the present invention. FIG. 3 is a sectional view of the wide-angle illumination device 10 according to the first embodiment of the present invention. The wide-angle illumination device 10 includes a base 12, a first light guiding module 14 and two second light guiding modules 16. The base 12 has a central region 18 and two lateral regions 20; the two lateral regions 20 are respectively disposed on opposite positions around the central region 18. Amounts of the first light guiding module 14 and the second light guiding module 16 are not limited to the embodiment shown in FIG. 1 to FIG. 3, and depend on design demand. The first light guiding module 14 is disposed on the central region 18, and the second light guiding module 16 is disposed on the lateral region 20.

The wide-angle illumination device 10 utilizes the first light guiding module 14 and the second light guiding module 16 to diffuse optical signals generated by light emitting modules, so as to form a wide-angle irradiation range. The wide-angle illumination device 10 can include a first light emitting module 22 and a second light emitting module 24; the first light emitting module 22 is disposed on the central region 18, and the second light emitting module 24 is disposed on the lateral region 20. The first light guiding module 14 is matched with the first light emitting module 22 to guide a first optical signal S1 generated by the first light emitting module 22 toward a front of the base 12, such as the front space above an upper surface of the base 12 used to hold the light guiding modules and the light emitting modules. The second light guiding module 16 is matched with the second light emitting module 24 to guide a second optical signal S2 generated by the second light emitting module 24 out of an end of the base 12, such as outer space nearby a right side and a left side of the base 12.

In the embodiment of the present invention, the base 12 can be designed as a strip-typed unit, and the central region 18 and the lateral region 20 are arranged along a longitudinally structural direction D1 of the strip-typed unit. The first light guiding module 14 guides an irradiation range of the first optical signal S1 slanted toward a planar normal vector V of the strip-typed unit, and the second light guiding module 16 guides an irradiation range of the second optical signal S2 slanted along the longitudinally structural direction D1, so that the first light guiding module 14 and the second light guiding module 16 can respectively guide the first optical signal S1 emitted by the first light emitting module 22 and the second optical signal S2 emitted by the second light emitting module 24 to form the one hundred and eighty degrees irradiation range. Further, due to an arc structure of the second light guiding module 16, the second optical signal S2 emitted by the second light emitting module 24 can be guided by the second light guiding module 16 to make the irradiation range cover a rear of the end of the base 12, such as the rear space behind two sides of a lower surface (which is not used to support the light guiding modules and the light emitting modules) of the base 12. Thus, the irradiation range of the wide-angle illumination device 10 can be greater than one hundred and eighty degrees.

The first light guiding module 14 can optionally include a plurality of first light guiding sub-components 26 respectively having irradiation ranges with different widths, and respectively disposed on a plurality of sub-regions 28 inside the central region 18. Among the plurality of first light guiding sub-components 26, some of the first light guiding sub-components 26 located at opposite positions can have the irradiation ranges with identical widths. As the embodiment shown in FIG. 1 to FIG. 3, the first light guiding sub-components 26 having symmetric forms and located on a middle of the base 12 can provide the irradiation range around 0~50 degrees, and the first light guiding sub-components 26 having asymmetric forms and located by the side of the symmetric forms can provide the irradiation range around 50~75 degrees. In addition, the second light guiding module 16 can provide the irradiation range around 75~90 degrees, so the irradiation range of the wide-angle illumination device 10 can be equal to or greater than one hundred and eighty degrees. Structural parameters of the light guiding sub-component are not limited to the above-mentioned embodiment, and depend on design demand.

The wide-angle illumination device 10 may further includes a third light guiding module 30 disposed on the base 12 and covering the central region 18 and the lateral region 20. The third light guiding module 30 is utilized to constrain the irradiation ranges of the first optical signal S1 and the second optical signal S2 along two sides of the base 12, which means the irradiation ranges of the first optical signal S1 and the second optical signal S2 along a transversely structural direction D2 of the base 12 (such like the strip-typed unit) can be constrained for preferred intensity of illumination. The first light guiding module 14, the second light guiding module 16 and the third light guiding module 30 can be monolithically integrated with the base 12; however, the foresaid light guiding modules may be detachably assembled with each other or detachably assembled with the base 12, which depend on design demand.

Figure 4:
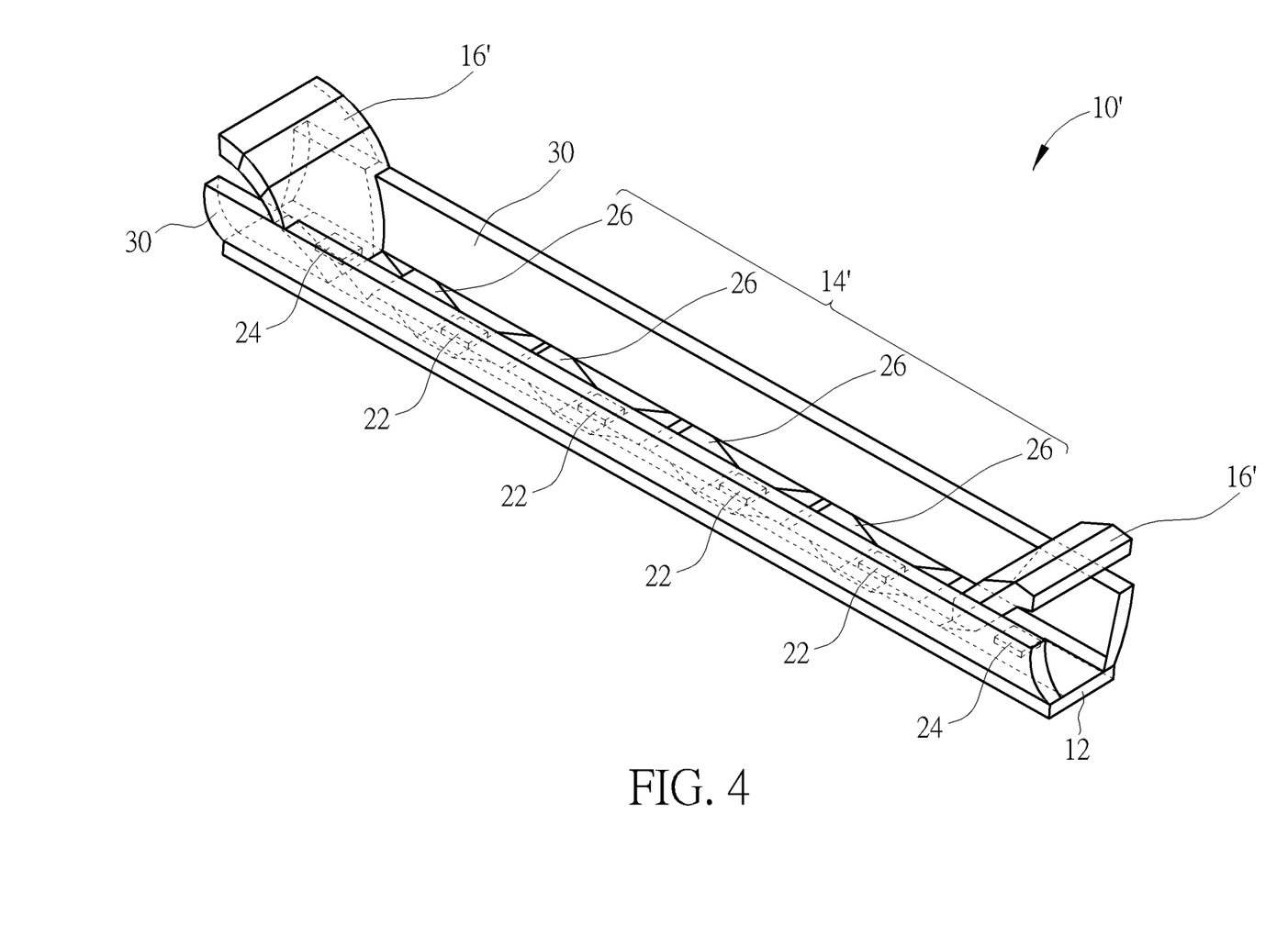
FIG. 4 is a diagram of a wide-angle illumination device according to a second embodiment of the present invention.
Figure 5:
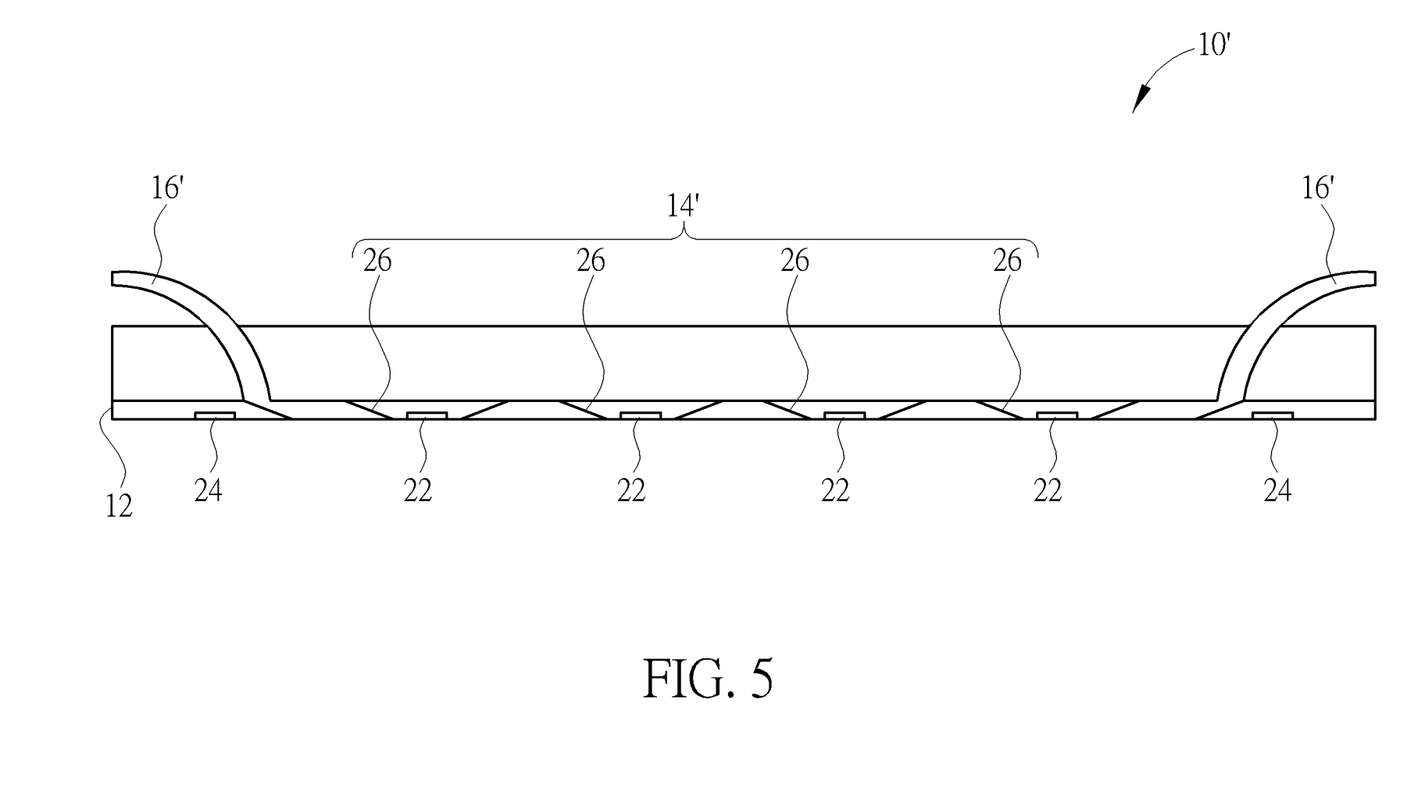
FIG. 5 is a sectional view of the wide-angle illumination device according to the second embodiment of the present invention.
Figure 6:
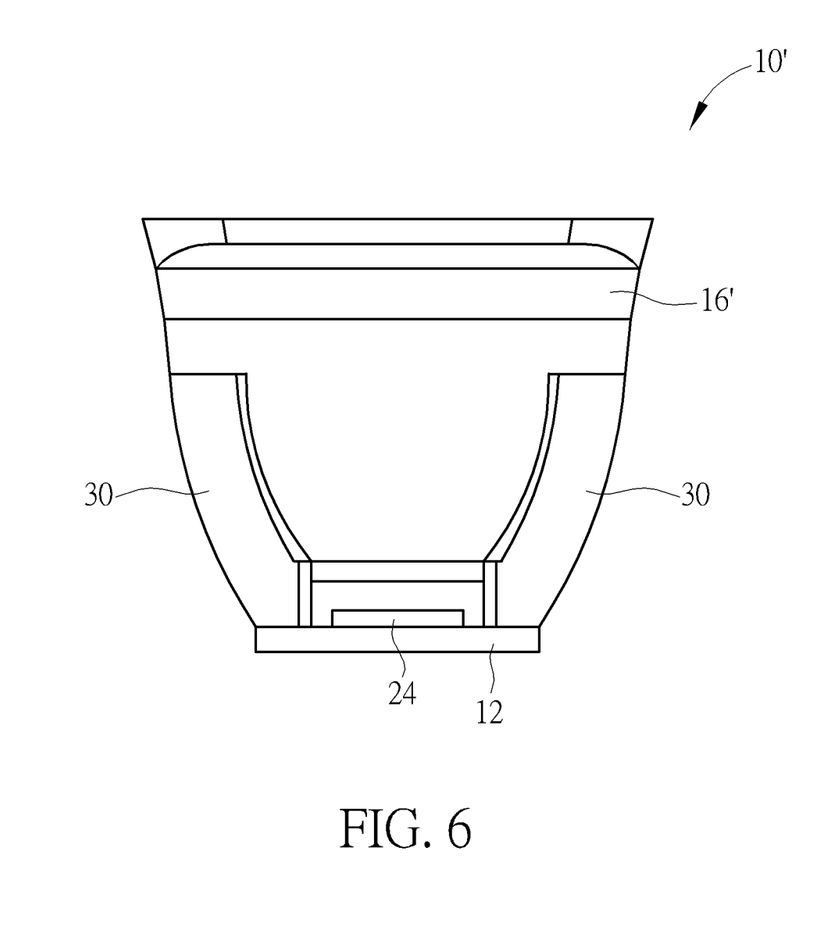
FIG. 6 is a front view of the wide-angle illumination device according to the second embodiment of the present invention.

Please refer to FIG. 4 to FIG. 6. FIG. 4 is a diagram of a wide-angle illumination device 10' according to a second embodiment of the present invention. FIG. 5 is a sectional view of the wide-angle illumination device 10' according to the second embodiment of the present invention. FIG. 6 is a front view of the wide-angle illumination device 10' according to the second embodiment of the present invention. In the second embodiment, elements having the same numerals as one of the first embodiment have the same structures and functions, and a detailed description is omitted herein for simplicity. Difference between the second embodiment and the first embodiment is: the first light guiding module 14 of the wide-angle illumination device 10 includes the first light guiding sub-component 26 with symmetric and asymmetric forms, but the first light guiding module 14' of the wide-angle illumination device 10' in the second embodiment preferably includes the light guiding sub-component with the symmetric forms. Further, the second light guiding module 16' of the wide-angle illumination device 10' can be stretched out of inner space of the third light guiding module 30, and has a shape different from the second light guiding module 16 of the wide-angle illumination device 10.

In the first embodiment and the second embodiment of the present invention, at least one of the first light guiding modules 14 and 14' and the second light guiding modules 16 and 16' can be designed as an asymmetric light guiding structure. The asymmetric light guiding structure is utilized to turn aside a transmission direction of the first optical signal S1 or the second optical signal S2, so the said transmission direction can be not parallel to the planar normal vector V of the base 12 for changing irradiation angles and the irradiation ranges. As shown in FIG. 3, the asymmetric light guiding structure has two light guiding walls 32a and 32b, and an inclined angle θ1 between the light guiding wall 32a and a bottom (which can be represented as an upper surface of the base 12) of the asymmetric light guiding structure is different from an inclined angle θ2 between the light guiding wall 32b and the foresaid bottom, so as to modulate the irradiation angle and the irradiation range of the optical signal. Besides, the light guiding walls 32a and 32b may respectively have refractive coatings with different reflection coefficients for modulation of the optical signal.

In the embodiments of the present invention, the light guiding walls 32a and 32b of the first light guiding sub-component 26 of the first light guiding modules 14 and 14' are disposed on the base 12 and utilized to guide the first optical signal S1 toward the front or upper space of the base 12. The first light guiding sub-components 26 located at different positions can include the light guiding walls having different or similar inclined angles. The second light guiding modules 16 and 16' may include a light guiding wall 34 disposed on the base 12; the light guiding wall 34 not only can guide the second optical signal S2 out of two ends of the base 12, but also can guide the second optical signal S2 toward the rear behind the two ends of the base 12. As shown in FIG. 3 and FIG. 5, the second light emitting module 24 is disposed on position of the base 12 close to the light guiding walls 34 of the second light guiding modules 16 and 16', and the first light emitting module 22, which corresponds to the first light guiding sub-components 26 of the first light guiding modules 14 and 14' located at opposite position, is disposed by the light guiding wall 32a of the base 12 far from the lateral region 20 optionally.

Therefore, the wide-angle illumination device of the present invention can utilize the first light guiding module and the second light guiding module having dissimilar irradiation ranges to guide the optical signals emitted by the first light emitting module and the second light emitting module respectively toward different irradiation angles and ranges. For example, the two first light guiding sub-components in middle of the first light guiding module can have the wider irradiation range mainly utilized to fill light in the central region via diffusion; the two first light guiding sub-components at the sides can have the gathered irradiation range utilized to slightly compensate the light in the central region; the second light guiding module can have the irradiation range focused on two ends of the base, so that the central region is slightly irradiated to form the uniform irradiation range equal to or greater than one hundred and eighty degrees on a single plane (which means the front above the base) along the longitudinally structural direction of the base. Comparing to the prior art, the present invention uses the single wide-angle illumination device to form the large scale irradiation range, and has no drawbacks of complicated light distribution, expensive hardware cost and difficult assembling procedures of the conventional illuminating device.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A wide-angle illumination device comprising:
   a base having a central region and two lateral regions, the two lateral regions being respectively disposed on opposite positions around the central region, a first light emitting module being disposed on the central region, and two second light emitting modules being respectively disposed on the two lateral regions;
   a first light guiding module disposed on the central region and matched with the first light emitting module, so as to guide a first optical signal emitted by the first light emitting module toward a front of the base; and
   two second light guiding modules disposed on the two lateral regions and respectively matched with the second light emitting modules, each of the two second light guiding modules being utilized to guide a second optical signal emitted by a corresponding second light emitting module out of an end of the base, wherein at least one of the first light guiding module and the two second light guiding modules are an asymmetric light guiding structure.

2. The wide-angle illumination device of claim 1, wherein the base is a strip-typed unit, the central region and the two lateral regions are arranged along a longitudinally structural direction of the strip-typed unit, the first light guiding module guides an irradiation range of the first optical signal slanted toward a planar normal vector of the strip-typed unit, and each of the two second light guiding modules guides an irradiation range of the second optical signal slanted along the longitudinally structural direction.

3. The wide-angle illumination device of claim 1, wherein an amount of irradiation ranges of the first light guiding module and the two second light guiding modules is equal to or greater than 180 degrees.

4. The wide-angle illumination device of claim 1, wherein the first light guiding module comprises a plurality of first light guiding sub-components respectively having irradiation ranges with different widths.

5. The wide-angle illumination device of claim 4, wherein the central region comprises a plurality of sub-regions where on the plurality of first light guiding sub-components is respectively disposed, and some of the first light guiding sub-components located at symmetrical positions have the irradiation ranges with identical widths.

6. The wide-angle illumination device of claim 1, wherein irradiation ranges of the two second light guiding modules cover a rear of the end of the base.

7. The wide-angle illumination device of claim 1, further comprising:
   a third light guiding module disposed on the base and covering the central region and the two lateral regions, and utilized to constrain irradiation ranges of the first optical signal and the second optical signal along two sides of the base.

8. The wide-angle illumination device of claim 7, wherein the base is a strip-typed unit, and the third light guiding module is utilized to constrain the irradiation ranges of the first optical signal and the second optical signal along a transversely structural direction of the strip-typed unit.

9. The wide-angle illumination device of claim 7, wherein the base, the first light guiding module, the two second light guiding modules and the third light guiding module are monolithically integrated with each other.

10. The wide-angle illumination device of claim 1, wherein the asymmetric light guiding structure comprises two light guiding walls respectively having refractive coatings with different reflection coefficients.

11. The wide-angle illumination device of claim 1, wherein the asymmetric light guiding structure comprises two light guiding walls, an inclined angle between one of the two light guiding walls and a bottom of the asymmetric light guiding structure is different from an inclined angle between the other light guiding wall and the bottom.

12. The wide-angle illumination device of claim 1, wherein the first light guiding module comprises two light guiding walls disposed on the base and utilized to guide the first optical signal toward the front of the base, each of the two second light guiding modules comprises a light guiding wall disposed on the base and utilized to guide the second optical signal out of the end of the base.

13. The wide-angle illumination device of claim 12, wherein the second light emitting modules are disposed on position of the base adjacent to the light guiding walls of the two second light guiding modules.

14. The wide-angle illumination device of claim 12, wherein the first light guiding module comprises a plurality of first light guiding sub-components, the first light emitting modules corresponding to some of the plurality of first light guiding sub-components located at opposite positions are disposed by one of the two light guiding walls on and the base far from the two lateral regions.

* * * * *